United States Patent [19]
Nakamoto et al.

[11] Patent Number: 5,684,584
[45] Date of Patent: *Nov. 4, 1997

[54] APPARATUS FOR ANALYZING CELLS IN URINE

[75] Inventors: Hiroyuki Nakamoto; Tokuhiro Okada, both of Hyogo-ken, Japan

[73] Assignee: TOA Medical Electronics Co., Ltd., Hyogo-ken, Japan

[*] Notice: The term of this patent shall not extend beyond the expiration date of Pat. No. 5,325,168.

[21] Appl. No.: 364,397

[22] Filed: Dec. 23, 1994

Related U.S. Application Data

[63] Continuation of Ser. No. 882,115, May 13, 1992, abandoned.

[30] Foreign Application Priority Data

May 14, 1991 [JP] Japan ................................ 3-108044

[51] Int. Cl.$^6$ ............................................. G01N 15/02
[52] U.S. Cl. ........................... 356/336; 356/73; 377/11
[58] Field of Search ............................ 356/335–343, 356/36, 39, 73, 318, 364, 243

[56] References Cited

U.S. PATENT DOCUMENTS

| | | | |
|---|---|---|---|
| 3,591,290 | 7/1971 | Zinner | 356/335 |
| 3,675,768 | 7/1972 | Legorreta-Sanchez | 356/39 |
| 3,883,247 | 5/1975 | Adams | 356/39 |
| 3,916,197 | 10/1975 | Fulwyler | 356/335 |
| 4,021,117 | 5/1977 | Gohde et al. | 356/39 |
| 4,263,508 | 4/1981 | Leary et al. | 356/335 |
| 4,288,162 | 9/1981 | Sakamoto et al. | 356/335 |
| 4,338,024 | 7/1982 | Bolz et al. | |
| 4,434,647 | 3/1984 | Whitcomb et al. | 356/243 |
| 4,661,913 | 4/1987 | Wu et al. | |
| 4,765,737 | 8/1988 | Harris et al. | 356/73 |
| 4,788,443 | 11/1988 | Furuya | 356/336 |
| 4,827,144 | 5/1989 | Zaitsu et al. | 356/336 |
| 4,850,707 | 7/1989 | Bowen et al. | 356/336 |
| 4,986,657 | 1/1991 | Obe | 356/73 |
| 5,047,963 | 9/1991 | Kosaka | 356/339 |
| 5,059,395 | 10/1991 | Brittenham et al. | 356/335 |

FOREIGN PATENT DOCUMENTS

| | | |
|---|---|---|
| 0138591 | 4/1985 | European Pat. Off. . |
| 0335001 | 10/1989 | European Pat. Off. . |
| 61-71337 | 4/1986 | Japan . |
| 3-52573 | 8/1991 | Japan . |
| 2107548 | 4/1983 | United Kingdom . |

*Primary Examiner*—Hoa Q. Pham
*Attorney, Agent, or Firm*—Fish & Richardson PC

[57] ABSTRACT

The present invention relates to an apparatus for automatically analyzing cells in urine using flow cytometry. The present invention includes means for converting scattered-light signals indicative of individual cells in a urine specimen into corresponding pulse signals, means for converting the pulse width of each pulse signal resulting from the aforementioned conversion into cell-diameter data in accordance with known cell diameters, and means for classifying and enumerating various cells in the urine in correlation with each item of cell-diameter data resulting from the conversion.

5 Claims, 5 Drawing Sheets

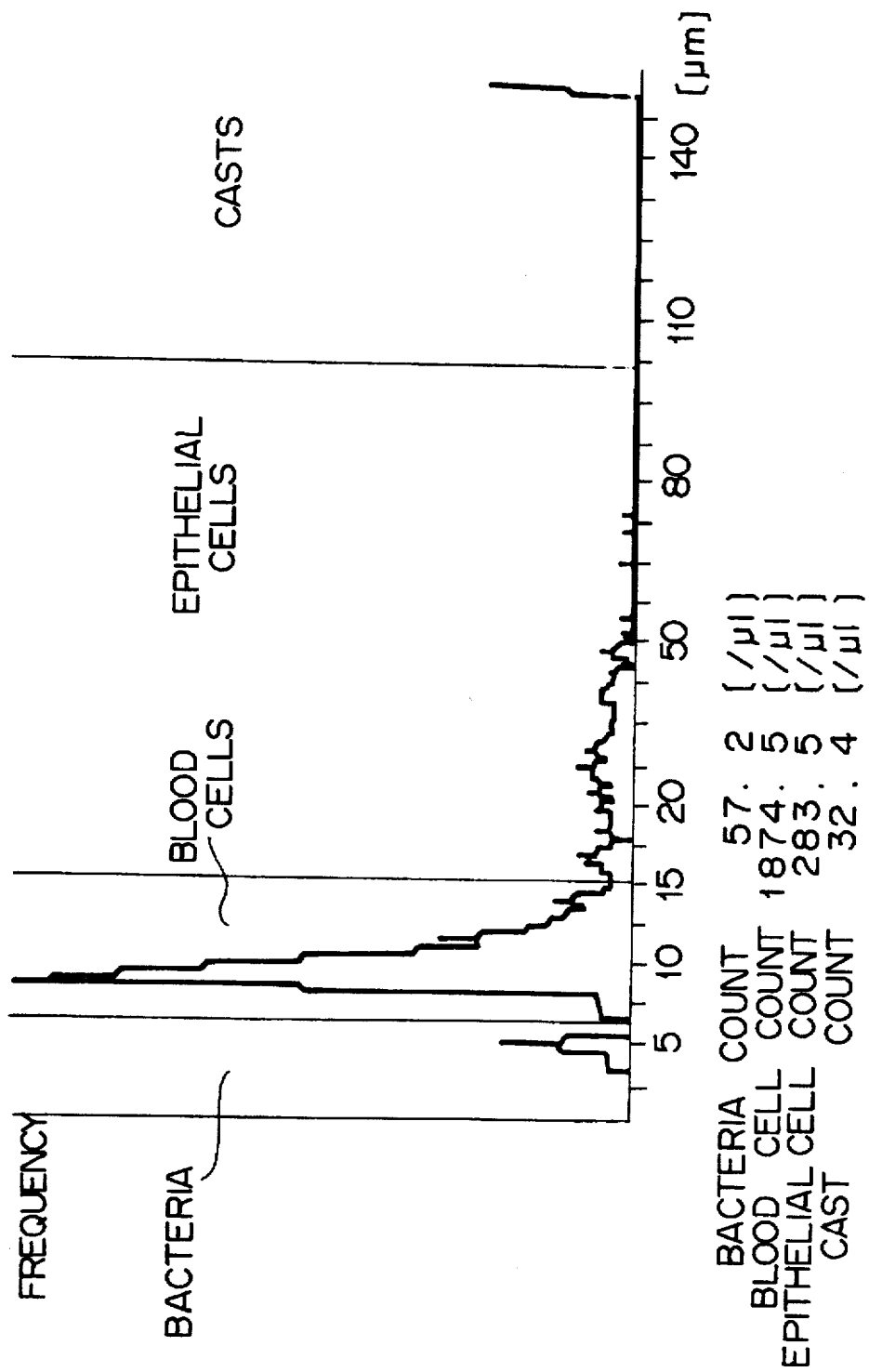

APPARATUS FOR ANALYZING CELLS IN URINE

This application is a continuation of U.S. application Ser. No. 07/882,115, filed May 13, 1992, now abandoned.

BACKGROUND OF THE INVENTION

1. Field of the Invention

This invention relates to an apparatus which uses flow cytometry to classify and enumerate cells such as blood cells, epithelial cells, casts and bacteria contained in urine.

2. Description of the Prior Art

Examination of urine content has long been carried out and is still of great importance. For example, a screening test for kidney failure can be conducted based upon the presence of erythrocytes, leukocytes, epithelial cells, casts and bacteria in urine. Measurement of erythrocytes is important in terms of determining whether hemorrhage has occurred in the tract from the slomerulus to the urethra of the kidney. The appearance of leukocytes is considered to be a possible indication, of a kidney disorder such as pyelonephritis, and detection thereof is important in early discovery of inflammation and infection. Furthermore, by examining cast and erythrocyte morphology, the origin of such inflammation and infection, namely the abnormal parts of the body, can be surmised.

In this specification, the word "cell" shall be used as a generic term for an erythrocyte, epithelial cell, cast and bacterium.

Conventional methods of analyzing cells in urine include (a) visual examination based upon microscopy and (b) automatic measurement using a combination of a flat sheath flow and image processing technology.

Method (a) involves centrifuging a urine specimen, preparing a slide sample of the matter of sediment and observing, classifying and counting cells under a microscope.

Method (b), an example of which is disclosed in the specification of Japanese Patent Application Laid-Open (KOKAI) No. 57-500995 or U.S. Pat. No. 4,338,024, involves using a video camera to capture an image of a urine specimen made to flow as an extremely flat stream within a sheathing solution employed as an outer layer, and subjecting the still picture obtained to image processing, whereby the images of the cells in the specimen are extracted and displayed.

However, both of the foregoing methods exhibit certain drawbacks. Specifically, method (a) which relies upon a microscope entails considerable labor for such pretreatments as centrifugal separation and staining. In addition, cells may be damaged in the centrifuging process and there are disparities in concentration from one specimen to another.

The apparatus which uses method (b) is itself high in cost owing to reliance upon image processing, and the processing speed is low. Furthermore, the advantage of automation afforded by the apparatus of method (b) merely displays the images upon roughly classifying the imaged components based upon their size, and it is required that classification process be performed by a human being while the display is observed. Thus, the automatic classification and enumeration of cell components is not possible.

Further, since the amount of the urine specimen measured according to the methods (a) and (b) is very small, a drawback is that casts, the discovery of the presence of which is very important, cannot be discovered in the urine sediment. Specifically, the low frequency of the presence of cast in such that usually only several tens thereof are present per milliliter.

Another problem is that since the types of components in urine sediment are numerous and differ widely in size from one specimen to another, and in view of the fact that the degree of cell damage can be considered to be large, it is believed that analysis of urine sediment is not possible using flow cytometry.

SUMMARY OF THE INVENTION

Accordingly, the present invention seeks to improve upon the foregoing shortcomings and its object is to provide an apparatus for analyzing cells in urine, in which a large quantity of a urine specimen can be used to analyze that urine, the number of various cells (blood cells, epithelial cells, casts and bacteria, etc.) detected in the specimen can be greatly increased to enable more precise analysis of cells in urine, the process from drawing of the urine specimen into the apparatus to display of the analytical results can be fully automated to eliminate the need for any human intervention, the processing speed can be raised and the cost of the apparatus can be kept low.

According to the present invention, the foregoing object is attained by providing an apparatus for analyzing cells in urine characterized in that scattered-light signals indicative of individual cells in a urine specimen are converted into respective pulse signals, the pulse width of each pulse signal resulting from the aforementioned conversion is converted into cell-diameter data in accordance with known cell diameters, and various cells contained in the urine are classified and counted in conformity with each item of cell-diameter data resulting from the conversion.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 9 is a diagram showing the results of measurement according to an embodiment of the invention.

DETAILED DESCRIPTION OF THE PREFERRED EMBODIMENT

A preferred embodiment of an apparatus for analyzing cells in urine according to the present invention will now be described with reference to the drawings.

Figure 1:
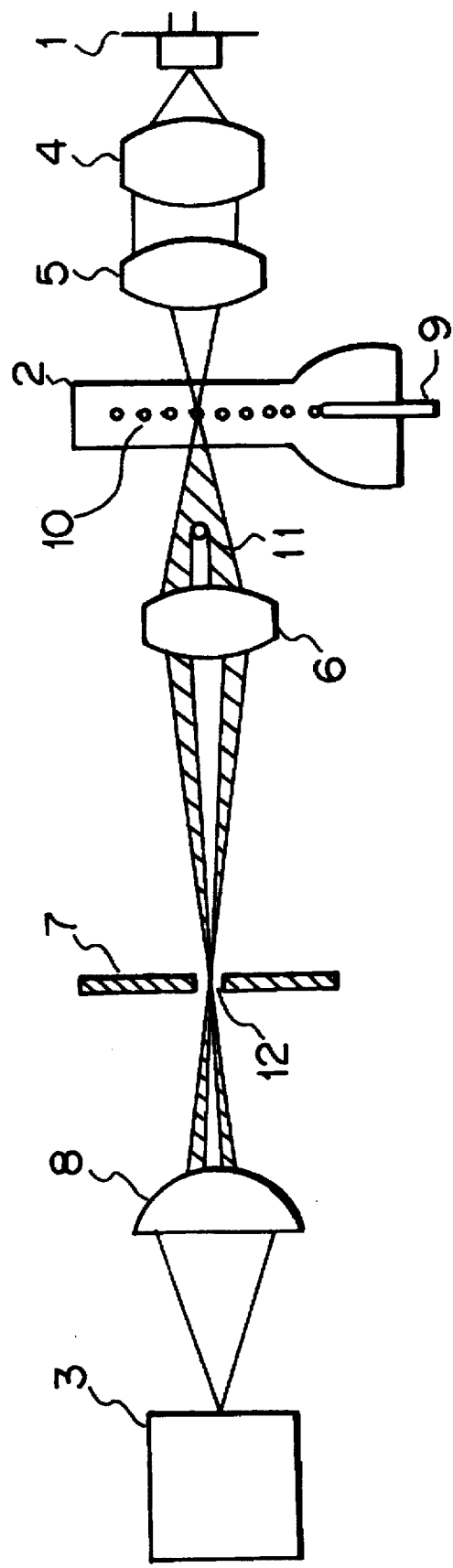
FIG. 1 is a block diagram showing the arrangement of the principal elements of an optical system embodying the present invention.

FIG. 1 is a block diagram showing the arrangement of the principal elements of an optical system embodying the present invention. As shown in FIG. 1, the optical system includes a light source 1 constituted by a semiconductor laser at one end of the system, a flow cell 2, a photodiode 3 at the other end of the system, a collimator 4 and a condenser lens 5 provided between the light source 1 and the flow cell 2, and a collector lens 6, a light shield 7 and a lens 8 provided between the flow cell 2 and the photodiode 3. A urine specimen flows into the flow cell 2 from a nozzle 9. Reference numeral 11 denotes a beam stopper.

Figure 2:
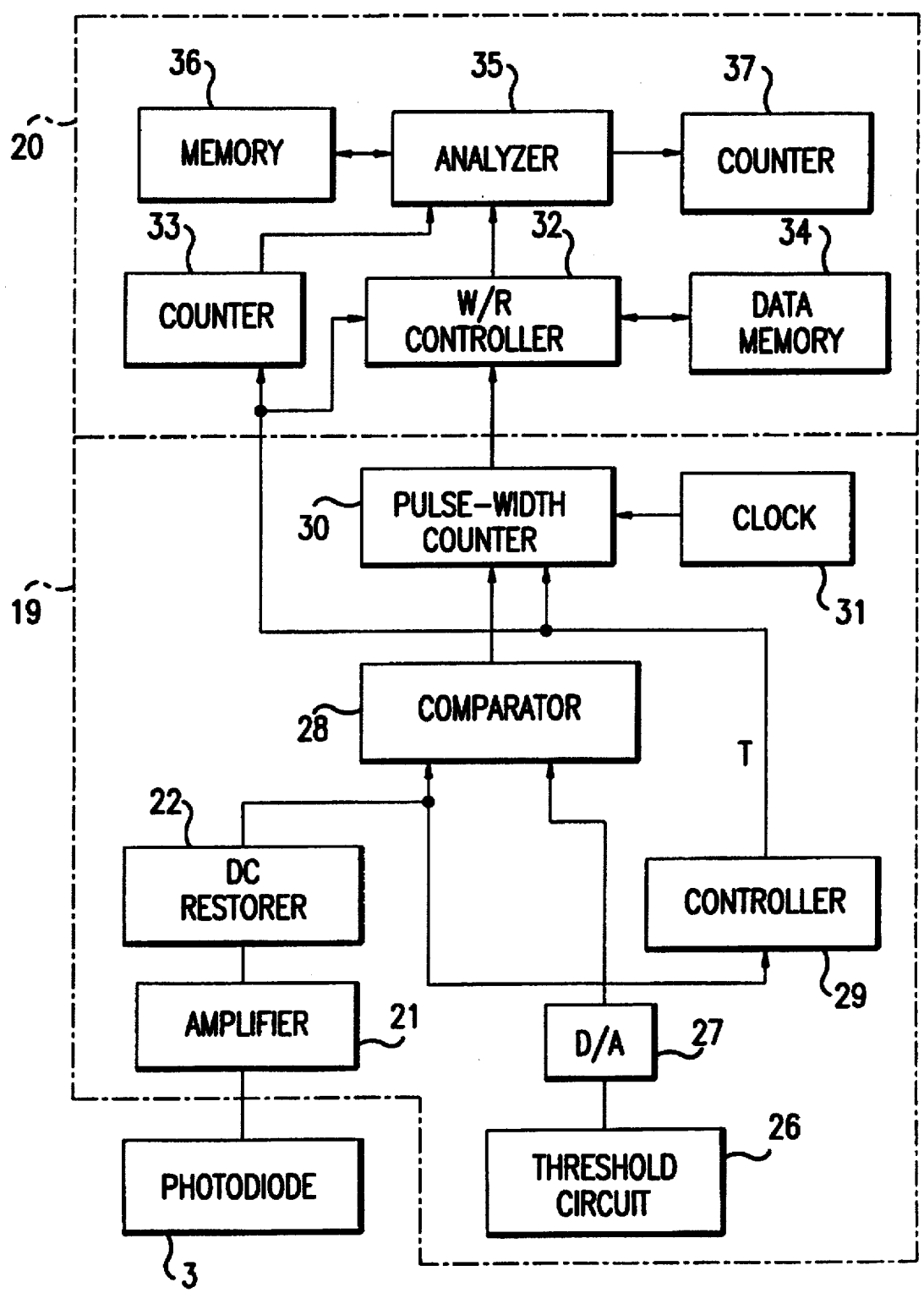
FIG. 2 is a block diagram illustrating the principal components of an electric circuit embodying the present invention.

FIG. 2 is a block diagram illustrating the principal components of an electric circuit embodying the present invention.

The circuitry of FIG. 2 is divided into a signal processing portion 19 and data processing portion 20. An output signal from the photodiode 3 is connected to an amplifier 21 in the signal processing portion 19, and the output of the amplifier 21 is connected to a DC (direct-current) restorer 22. A threshold circuit 26 is connected to a digital/analog converter circuit (hereinafter referred to simply as a "D/A converter") 27, the output of which is connected to the reference input of a comparator 28. The output of the DC restorer 22 is connected to the comparator 28 at its other input terminal, namely the terminal whose input is to be compared with the reference. The output of the comparator 28 is connected to a pulse-width counter 30, to which a clock signal from a clock signal generating circuit 31 is applied as an input. The output of the DC restorer 22 is further connected to a control circuit 29.

The output of the pulse-width counter 30 is connected to a control circuit 32, which is for controlling a read/write operation. A trigger signal T is connected to the control circuit 32 and a counter 33. A memory circuit 34 for storing data indicative of individual cells is connected to the control circuit 32. The memory circuit 34 is connected, via the control circuit 32, to a data analyzing circuit 35 which classifies and enumerates cells. The output of the counter 33 also is connected to the data analyzing circuit 35. A counter 37, which counts the number of each type of cell, is connected to the data analyzing circuit 35. The data processor 20 further includes a memory circuit 36 which stores the control program of the apparatus, cell-diameter conversion values, cell judgment values, etc.

Figure 3:
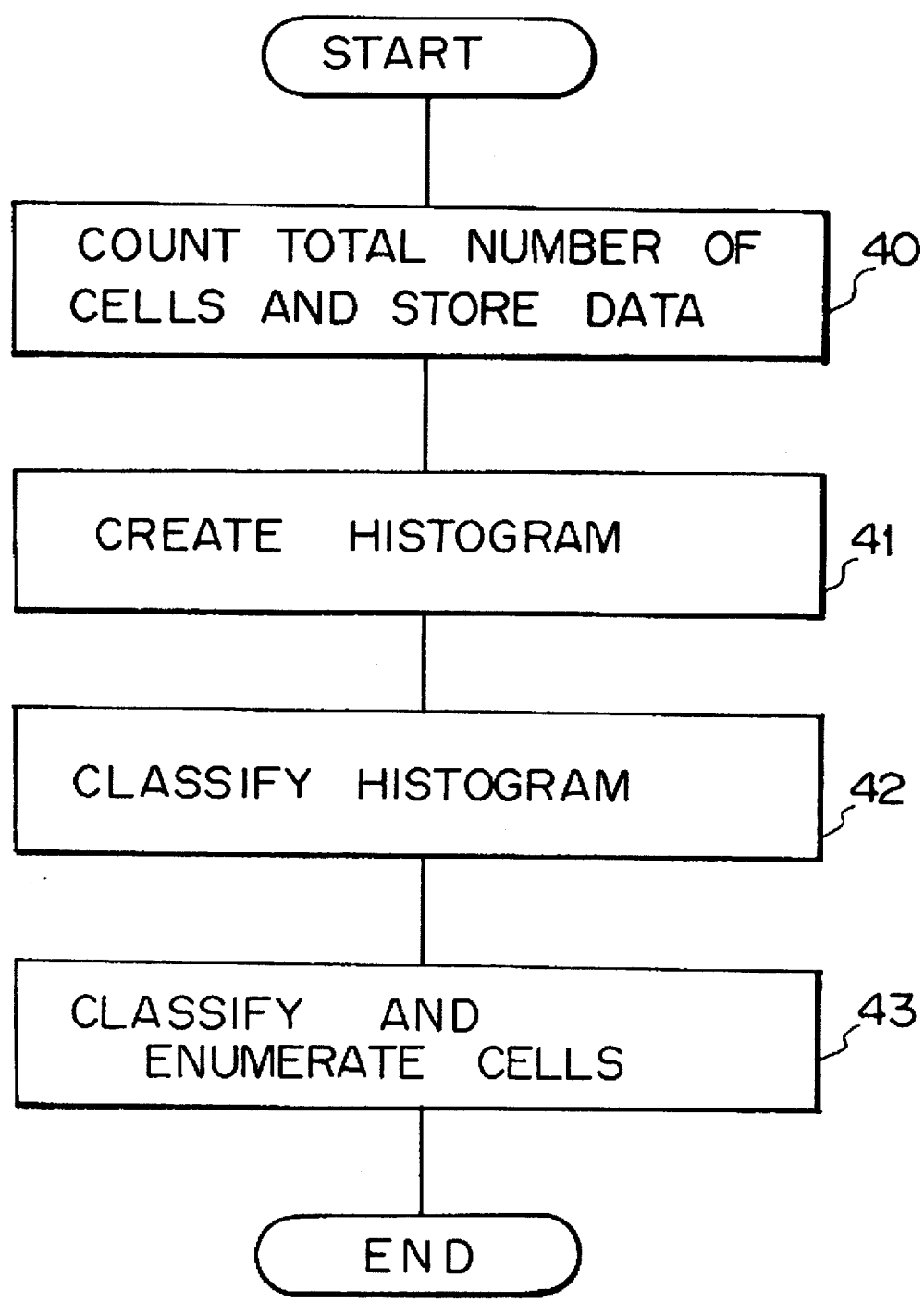
FIG. 3 is a flowchart illustrating operation of the embodiment.

FIG. 3 is a flowchart illustrating the operation of the electrical circuitry according to this embodiment. This flowchart will be referred to later.

The operation which characterizes the embodiment of the invention constructed as set forth above will now be described.

In order to stabilize pH and osmotic pressure, a reagent for this purpose is mixed with the original solution of the urine specimen. The resulting urine specimen mixture containing the reagent is discharged from the nozzle 9, and a sheathed flow is formed by causing a sheathing solution to flow along the periphery of the urine stream. As a consequence, cells 10 (blood cells, epithelial cells, casts and bacteria, etc.) in the urine specimen flow in an ordered array such as in single file through a narrow zone at the central portion of the flow cell 2, as shown in FIG. 1. The laser light from the light source 1 is formed into a collimated light beam by the collimator 4, and the collimated light beam is then condensed by the condenser lens 5 so as to irradiate the narrow flow zone of the flow cell with an elliptical beam spot that is slender in the direction of flow and broad in the direction perpendicular to the flow direction.

The present invention is directed toward measurement of cells in urine, namely components of urine sediment. In order to obtain more detailed information from the group of cells carried by urine, the thickness of the narrow flow zone should be set to be comparatively small in comparison with the sizes of the cells. As for the dimensions of the irradiating elliptical beam spot at the constricted portion of the specimen stream, a suitable value for the minor axis of the ellipse is 1–20 μm (8 μm in this embodiment). It will suffice to make the major axis of the ellipse large enough to fully extend across the width of the slender specimen stream in the narrow flow zone.

Thus, the cells 10 in the slender specimen stream are irradiated with the laser light. Transmitted laser light which has passed through the flow cell intact without striking the cells is blocked by a beam stopper 11. Forward-scattered light emitted from an irradiated cell at a narrow angle is condensed by the collector lens 6, the condensed light passes through a pin hole 12 of the shield 7, the emergent light is further condensed by the lens 8, the resulting light is converted into an electric signal by the photodiode 3, and the photodiode 3 produces an output signal indicative of the forward-scattered light. Output waveforms of this forward-scattered light signal from the photodiode 3 are as illustrated in the waveform diagrams of FIGS. 4 through 8, in which time is plotted along the horizontal axis and voltage along the vertical axis.

Figure 4:
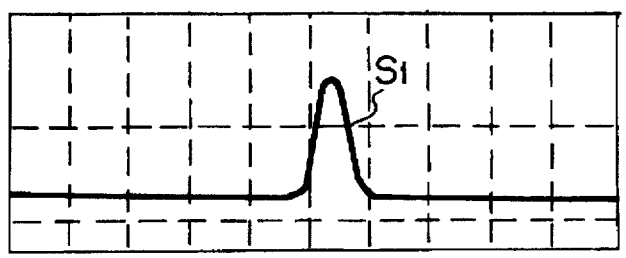
FIG. 4 is a waveform diagram illustrating a forward-scattered light signal from an erythrocyte.

FIG. 4 shows a signal waveform indicative of forward-scattered light from an erythrocyte. Since erythrocytes are small in size and regular in shape, a forward-scattered light signal $S_1$ having a single peak is obtained.

Figure 5:
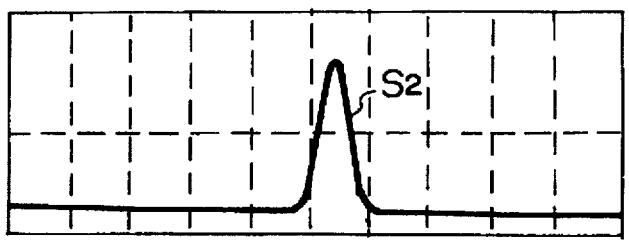
FIG. 5 is a waveform diagram illustrating a forward-scattered light signal from a leukocyte.

FIG. 5 shows a signal waveform indicative of forward-scattered light from a leukocyte. Leukocytes are large but are of the same size or slightly larger than erythrocytes, and a forward-scattered light signal $S_2$ similar to the forward-scattered light signal $S_1$ is obtained.

Figure 6:
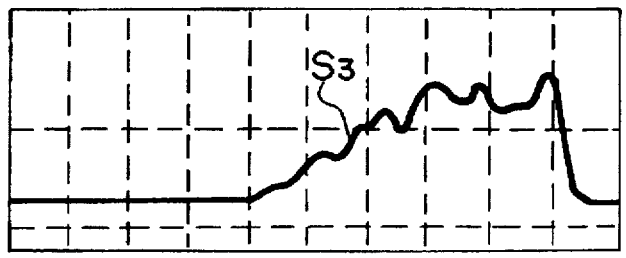
FIG. 6 is a waveform diagram illustrating a forward-scattered light signal from an epithelial cell.

FIG. 6 depicts a signal waveform indicative of forward-scattered light from an epithelial cell. Epithelial cells exist in a wide variety of sizes from large to small, but they are small in thickness and possess a complicated shape and internal structure. As a result, a forward-scattered light signal $S_3$ obtained exhibits a large width and a complicated waveform.

Figure 7:
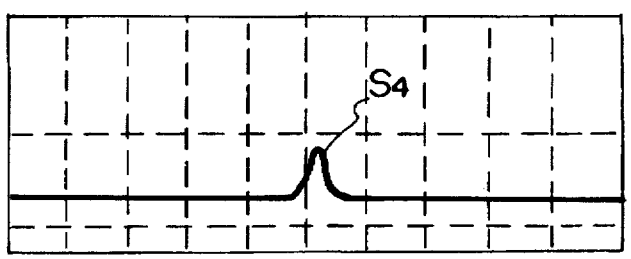
FIG. 7 is a waveform diagram illustrating a forward-scattered light signal from a bacterium.

FIG. 7 illustrates a signal waveform indicative of forward-scattered light from a bacterium. Since bacteria are small in comparison with blood cells and the like, a small forward-scattered light signal $S_4$ is obtained.

Figure 8:
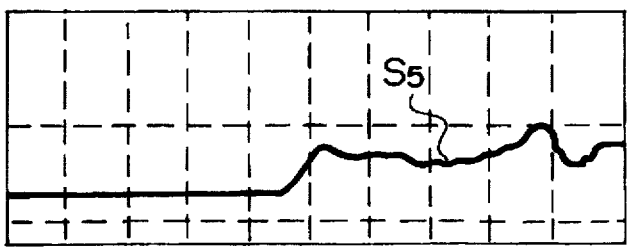
FIG. 8 is a waveform diagram illustrating a forward-scattered light signal from a cast.

FIG. 8 shows a signal waveform indicative of forward-scattered light from a cast. Since a cast has a size on the order of one hundred to several hundred microns, a forward-scattered light signal $S_5$ having a very large width is obtained.

Thus, the photodiode 3 produces a forward-scattered light signal for each of the variety of cells contained in the urine specimen. Each forward-scattered light signal is amplified by the amplifier 21 in the signal processor 19, and the amplified signal is applied to the DC restorer 22, which removes DC components and extracts the amplitude portion (namely the portion of the forward-scattered light signal). The resulting forward-scattered light signal from which the DC components have been removed is applied to the comparison input terminal of the comparator 28.

In order to eliminate the effects of contaminants such as dust particles contained in the urine specimen, the threshold circuit 28 is set beforehand to an appropriate threshold value. This threshold value is converted into an analog value by the D/A converter 27, and a voltage indicative of the analog value is applied to the reference input terminal of the comparator 28. Only a forward-scattered light signal which exceeds the threshold value is outputted by the comparator 28 in the form of square-wave. The square-wave signal enters the pulse-width counter 30, which counts the clock signal from the clock signal generator 31 for the duration of the square wave input. As a result, the forward-scattered light signal is converted into pulse-width data, which is outputted by the pulse-width counter 30. At this time the output of the DC restorer 22 enters the control circuit 29, which proceeds to detect the beginning and end of the forward-scattered light signal and control the duration of the pulse-width count performed by the pulse-width counter 30. Accordingly, each item of pulse-width data is data which corresponds to the cell diameter of each detected cell.

In accordance with the invention, a measurement is taken using latex particles of a known particle diameter before a urine specimen is measured. Then, from the pulse-width data acquired by this preliminary measurement of the latex particles and the known diameter of these particles, conversion values for the purpose of converting the above-mentioned pulse-width data into particle diameters are calculated and the conversion values are then stored in the memory circuit 36 beforehand as conversion values of cell diameter. Furthermore, each type of cell in the urine specimen is actually measured in advance under a microscope, and cell judgment values in which the sizes of the cells are statistically obtained based upon these actual measurements are also stored in the memory circuit 36.

The cell judgment values are 3–10 μm for erythrocytes, 3–15 μm for leukocytes, 15–150 μm for epithelial cells, 100 μm for casts and 1–3 μm for bacteria.

The pulse-width data is fed into the data processing portion 20 from the pulse-width counter 30 whenever the trigger signal T, which is generated at each cell flow-by, enters the data processor 20.

The data analyzer 35 converts each item of pulse-width data into a cell diameter based upon the aforementioned cell diameter conversion values, and the cell diameters obtained are stored cell by cell in the memory circuit 34 in accordance with control executed by the control circuit 32.

The counter 33 counts the cells in successive fashion. This operation is carried out until the entirety of the urine specimen has passed through the flow cell 2. The storage and counting operations are executed at step 40 in the flowchart of FIG. 3. When all of the urine specimen has passed through the flow cell 2, the total number of cells detected in the urine specimen is held in the counter 33, and the cell-diameter data for all cells detected in the urine specimen is stored in the memory circuit 34 on a cell-by-cell basis. Further, the data analyzer 35 creates and displays a histogram (step 41) of all detected cells, in which cell diameter (μm) is plotted along the horizontal axis. The data analyzer 35 reads the cell judgment values from the memory circuit 36, retrieves the histogram valleys in the vicinity of these cell judgment values and, on the basis of the valleys retrieved, classifies the histogram into a bacteria region, a blood-cell region, an epithelial cell region and a cast region (step 42). The results actually measured are illustrated in FIG. 9. Observing the histogram of FIG. 9 makes it possible for the user to judge the results of urinalysis in a simple manner. In order to perform a detailed analysis of the number of cells contained in the urine sample, the number of cells in each region of the divided histogram is counted by the counter 37 and the resulting numerical value is displayed below the histogram (step 43). Thus user may thus determine the results of highly accurate urinalysis.

Though the foregoing embodiment has been illustrated taking forward-scattered light as an example, it should be obvious that equally good results can be obtained using side-scattered light as well. If necessary, the display can be limited solely to that of the histogram or the numbers of cells counted.

The apparatus of the invention described above is so adapted that signals indicative of the scattered light from individual cells in a urine specimen are converted into corresponding pulse signals, and the pulse widths of the resulting pulse signals are converted into cell-diameter data in accordance with known cell diameters. Furthermore, the invention is so adapted that all cells detected in the urine specimen are enumerated as well as the cells in each divided region of the histogram.

As a result, a variety of cells such as blood cells, epithelial cells, casts and bacteria contained in urine can be classified automatically in conformity with the cell-diameter data obtained by conversion. In addition, the total number of cells in the urine specimen and the numbers of the individual types of cells in the specimen can be counted and displayed automatically and at high speed.

As many apparently widely different embodiments of the present invention can be made without departing from the spirit and scope thereof, it is to be understood that the invention is not limited to the specific embodiments thereof except as defined in the appended claims.

What is claimed is:

1. Apparatus for analyzing cells in a urine specimen, comprising:

means defining a constricted zone in which cells contained in the urine specimen may flow in single file;

means for irradiating with light the constricted zone; photoelectric converting circuit for converting light scattered by the cells into an electric signal output;

first-means for converting the electric signal output from said photoelectric converting circuit into pulse-width data;

second means for converting the pulse-width data obtained by the first converting means into cell-diameter data on the basis of cell-diameter values of individual cells measured in advance, wherein the second converting means derives the cell-diameter data solely from the pulse-width data;

cell classifying means for classifying and enumerating the cells in the urine specimen based upon cell judgment values, such that:

(a) a cell is classified as a blood cell when the cell diameter data is 3–15 μm;

(b) a cell is classified as an epithelial when the cell diameter data is 15–100 μm;

(c) a cell is classified as a cast cell or a epithelial when the cell diameter data is 100–150 μm;

(d) a cell is classified as a cast cell when the cell diameter data is greater than 150 μm;

(e) a cell is classified as a bacteria when the cell diameter data is 1–3 μm; and means for displaying results of classification and enumeration performed by cell classifying means.

2. The apparatus according to claim 1, the width of the cell flow in the direction of said flow is in the range of 1 μm to 20 μm.

3. The apparatus according to claim 1, wherein the cell classifying means includes:

means for creating a histogram that is based upon the cell-diameter data; and means for classifying the histogram into cell regions based upon valleys of the histogram at positions in the vicinity of cell-diameter values of individual cells actually measured in advance.

4. A method of analyzing cells in urine comprising (i) converting scattered light signals indicative of individual cells in a urine specimen into respective pulse signals, (ii) providing cell-diameter data solely from pulse width data by converting the pulse width of each pulse signal into cell-diameter data in accordance with known cell diameter, and (iii) classifying and counting various cells contained in the urine based upon cell judgment, such that (a) a cell is classified as a blood cell when the cell diameter data is 3–15 μm;

(b) a cell is classified as an epithelial when the cell diameter data is 15–100 μm;

(c) a cell is classified as a cast cell or an epithelial when the cell diameter data is 100–150 μm;

(d) a cell is classified as a cast cell when the cell diameter data is greater than 100 μm;

(e) a cell is classified as a bacteria when the cell diameter data is 1–3 μm.

5. The method of according to claim 4, the width of the cell flow in the direction of said flow is in the range of 1 μm to 20 μm.

* * * * *